(12) United States Patent
Takatsuji et al.

(10) Patent No.: US 8,373,021 B2
(45) Date of Patent: Feb. 12, 2013

(54) IMPROVING DISEASE RESISTANCE IN PLANTS BY INTRODUCING TRANSCRIPTION FACTOR GENE

(75) Inventors: Hiroshi Takatsuji, Tsukuba (JP); Shoji Sugano, Tsukuba (JP); Masaki Shimono, Tsukuba (JP); Chang-Jie Jiang, Tsukuba (JP); Hisatoshi Kaku, Tsukuba (JP)

(73) Assignee: National Institute of Agrobiological Sciences, Ibaraki (JP)

( * ) Notice: Subject to any disclaimer, the term of this patent is extended or adjusted under 35 U.S.C. 154(b) by 648 days.

(21) Appl. No.: 11/919,864

(22) PCT Filed: May 26, 2006

(86) PCT No.: PCT/JP2006/310542
§ 371 (c)(1),
(2), (4) Date: Jan. 9, 2009

(87) PCT Pub. No.: WO2006/126671
PCT Pub. Date: Nov. 30, 2006

(65) Prior Publication Data
US 2010/0122374 A1 May 13, 2010

(30) Foreign Application Priority Data
May 26, 2005 (JP) .................................. 2005/154731

(51) Int. Cl.
C12N 15/82 (2006.01)
C12N 15/29 (2006.01)
(52) U.S. Cl. .................... 800/279; 536/23.6; 800/320
(58) Field of Classification Search .................... 800/279
See application file for complete search history.

(56) References Cited

U.S. PATENT DOCUMENTS

| 5,177,308 | A | 1/1993 | Barton et al. |
| 2003/0101481 | A1 | 5/2003 | Zhang et al. |
| 2006/0130177 | A1 | 6/2006 | Mori et al. |
| 2007/0275464 | A1 | 11/2007 | Kaku et al. |

FOREIGN PATENT DOCUMENTS

| EP | 0360750 | | 3/1990 |
| JP | 2-186925 | | 7/1990 |
| JP | 3-247220 | | 11/1991 |
| JP | 4-330233 | | 11/1992 |
| JP | 7-250685 | | 10/1995 |
| JP | 2003-88379 | | 3/2003 |
| JP | 2003-199448 | | 7/2003 |
| JP | 2004-329215 | | 11/2004 |
| JP | 2005-185101 | | 7/2005 |
| WO | WO02/50293 | | 6/2002 |
| WO | WO 0250293 | A2 * | 6/2002 |
| WO | WO2004/013331 | | 2/2004 |
| WO | WO2004/106512 | | 12/2004 |
| WO | WO2005/085444 | | 9/2005 |

OTHER PUBLICATIONS

Qui, Y., Jing, S., Fu, J., Li, L., Yu, D. Cloning and analysis of expression profile of 13 WRKY genes in rice. (2004) 49: 2159-2168.*
Xie et al. Annotations and functional analyses of the Rice WRKY gene superfamily reveal positive and negative regulators of abscisic acid signaling in aleurone cells (2005) Plant Phys. 137: 176-189.*
Anderson et al. Antagonistic interaction between absisic acid and jasmonic -ethylene signaling pathways modulates defense gene expression ans disease resistance in *Arabidopsis* (2004) The Plant Cell 16: 3460-3479.*
Guo et al. (2004) PNAS 101: 9205-9210.*
Song et al. (1995) Science 270: 1804-1806.*
Xie et al. (2005) Plant Physiology 137: 176-189.*
Anderson et al. (2004) The Plant Cell 16: 3460-3479.*
Yu et al. GenBank Accession No. AY870611 (2004).*
Zhang et al. GenBank Accession No. Q6IEN6 (2004).*
Datta et al. (1999) Theor. Appl. Genet. 98:1138-1145.*
Lee et al. (2003) Planta 216: 1043-1046.*
UniProt Accession No. Q5W6D6; Dec. 7, 2004.
EMBL Accession No. AK066255; Mar. 14, 2005.
Shimono, et al. Plant Cell Physiol. 2006; 47 (Suppl.): s83 [#236 (1pK14)].
European Patent Office Extended Search Report, dated Mar. 23, 2009, offered to further explain Ref. Nos. 13 and 17, as they are not submitted in English. If the Examiner requests a translation, the Applicant will submit same.
Asai, et al. Nature, Feb. 28, 2002; 415(6875): 977-83.
Chen, et al. Plant Physiol. Jun. 2002; 129(2): 706-16.
Eulgem, et al. Trends Plant Sci. May 2000; 5(5); 199-206.
Kalde, et al. Mol Plant Microbe Interact. Apr. 2003; 16 (4): 295-305.
Li, et al. Plant Cell. Feb. 2004; 16(2): 319-31. Epub Jan. 23, 2004.
Qui, et al. Chin Sci Bull. 2004; 49(20): 2159-68.
Robatzek, et al. Genes Dev. May 1, 2002: 16 (9): 1139-49.
Windhovel, et al. Plant Physiol. Jan. 1994; 104(1): 119-125.
Xie, et al. Plant Physiology, Jan. 2005; vol. 137(1): pp. 176-189. Epub Dec. 23, 2004.
Yu, et al. Plant Cell. Jul. 2001; 13(7): 1527-39.
Xu, et al., Plant Cell. May 2006; 18(5):1310-26. Epub Apr. 7, 2006.
Zheng, et al, Plant J. Nov. 2006; 48(4) :592-605. Epub Oct. 19, 2006.
Robatzek, et al, Plant J. Oct. 2001; 28(2): 123-33.
Mare, et al, Plant Mol Biol. May 2004; 55(3) : 399-416.

* cited by examiner

*Primary Examiner* — David T Fox
*Assistant Examiner* — Steven Bernacki
(74) *Attorney, Agent, or Firm* — Medlen & Carroll, LLP

(57) ABSTRACT

The present inventors analyzed genes involved in plant disease resistance. As a result, they discovered the transcription factor gene OsWRKY45, which is induced in leaf blades of rice plants by activating the systemic acquired resistance (SAR) that plants inherently have, i.e., by treating rice plants with benzothiadiazole (hereafter may be abbreviated as BTH), which is an agent thought to induce disease resistance in plants. It was further discovered that rice blast disease resistance and rice bacterial leaf blight resistance were markedly improved by reintroducing the gene into rice plants and constitutively expressing it.

8 Claims, 10 Drawing Sheets

FIG. 3
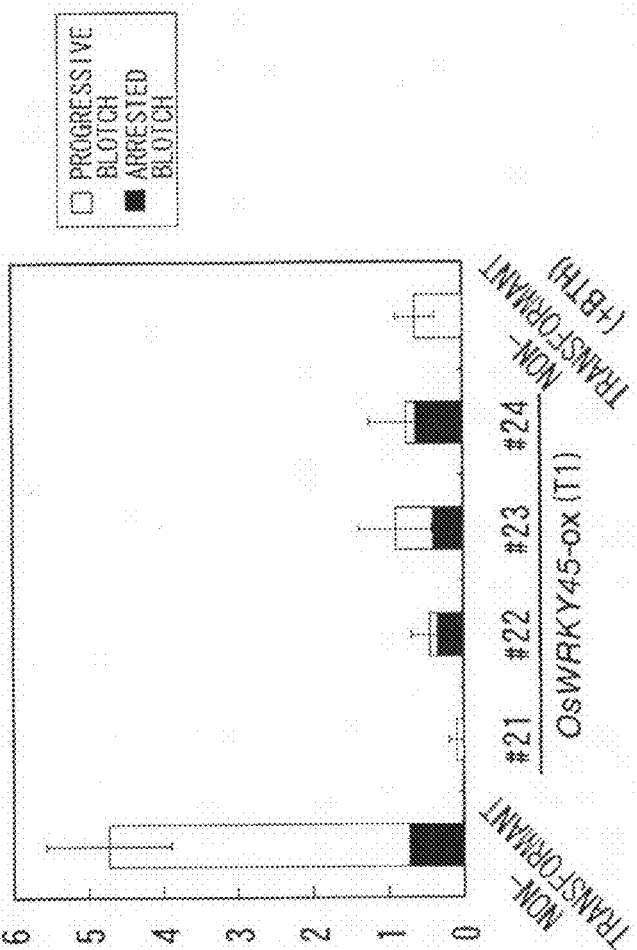
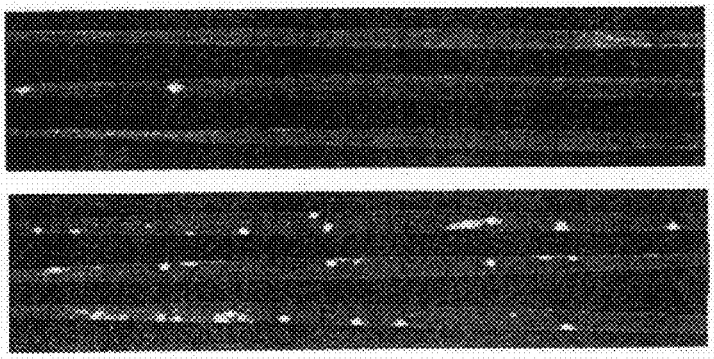

(A)

|  | FOLIAR AGE | PLANT LENGTH (cm) | TILLER NUMBER |
|---|---|---|---|
| CONTROL | 11.0 +/- 0.2 | 93.9 +/- 2.6 | 4.9 +/- 1.4 |
| #15 | 9.7 +/- 0.6 | 71.4 +/- 7.1 | 2.5 +/- 0.5 |
| #19 | 9.9 +/- 0.3 | 71.0 +/- 4.8 | 2.3 +/- 0.6 |
| #21 | 9.9 +/- 0.3 | 67.5 +/- 3.8 | 2.5 +/- 0.6 |
| #23 | 11.4 +/- 0.2 | 90.7 +/- 3.4 | 4.0 +/- 0.9 |
| #24 | 9.7 +/- 0.3 | 65.9 +/- 4.9 | 2.2 +/- 0.7 |

(B)

FIG. 9
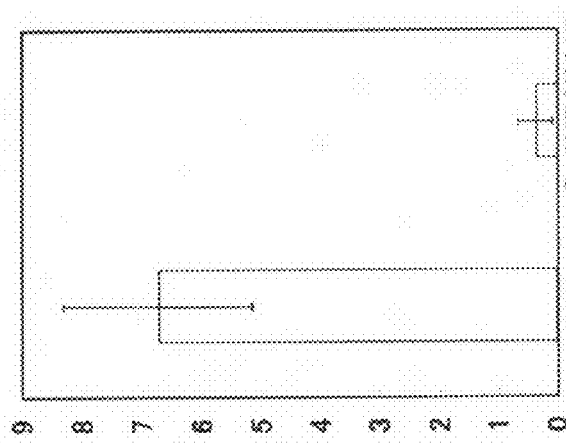
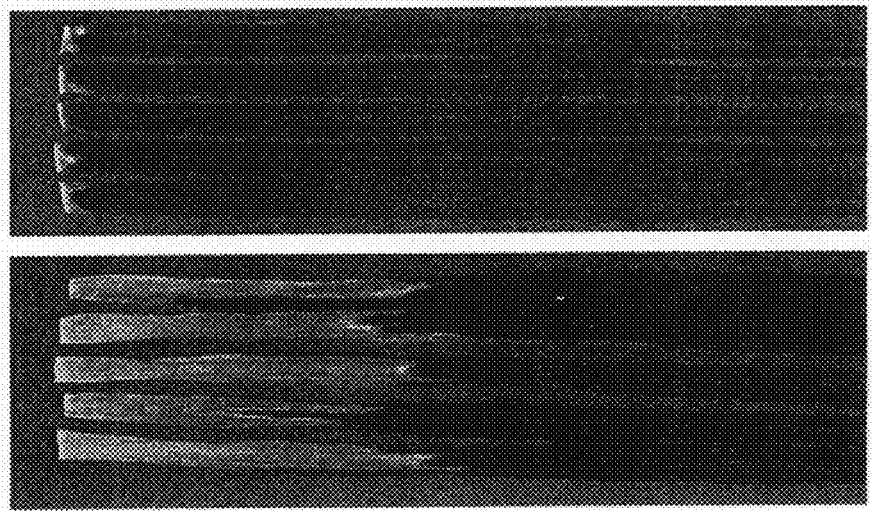

SEQUENCE LISTING

<160> NUMBER OF SEQ ID NOS: 4

<210> SEQ ID NO 1
<211> LENGTH: 1453
<212> TYPE: DNA
<213> ORGANISM: Oryza sativa

<400> SEQUENCE: 1

```
gggtgctttg agctccatca ccagctgagc tgcgaggaag agagagtgcg agagtgcgcg      60
gcagcggcag tgtagtgtca gtcactgggt gtgcgcttgc ttgcttggat tgaggatgac     120
gtcatcgatg tcgccggcgc cggcgccggc gtacgcgcag gtgatggagg acatggagaa     180
ggggaaggag ctggcggcgc agctgcaggg gctcctccgc gactcgccgg aggccggccg     240
cttcgtcgac cagattctcc acaccttctc ccgggcgatg cgggcgctcg acaaggcggc     300
ggtctccgcc gccggaggag aagggtcgga ggtgcagagc gaggtcacct gcggggcgg      360
ggccagcgcc ggcgggaaga ggaaagcccc cgccgccgac cggaaggcca actgccgcag     420
gaggacgcag caatcgtccg ggaattcggt ggtcgtcaag aacctcgacg acggccaggc     480
atggcgcaag tacgggcaga aggagatcca aaactccaag cacccaaagg cctacttccg     540
gtgcacgcac aagtacgacc agctgtgcac ggcgcagcgg caggtgcagc gctgcgacga     600
cgacccggcg agctacaggg tcacctacat cggcgagcac acctgccggg acccggccac     660
cgccccatc atcgcggcgc acgtcatcca ccaggtcgcc gccggcgaca cgacgacgg       720
ctgcggcggc ctccaagcgg ggtcccgcct catcagcttc gtcgccgcgc cggcggcgcc     780
agtagacgct gccgcggcgc cgacgaccag cacgatcacc acggtcaccg cgccgggccc     840
gctgctgcag ccgctcaagg tggagggcgg cgtcggctcg tccgaccagg aggaggtgct     900
gagcagcctc acgccggca gctccgcggc gcgcggcggc ggcggcggcg gcggagtcgc      960
gggtcccttc gggccggacc agggcgatgt cacgtcctcc ctgcactgga gctacgacgc    1020
cgtcgccggc atggagttct tcaagaacga cgaggttgtc ttcgatctgg acgacattat    1080
gggtttgagc ttttgatcac cgaagaatca tggatggaca cgggccgggt aaaacgatcg    1140
aaagaagatg gattccacgc gtgtgtacag aataattag cggcagcgcg atcttaatt      1200
tggaacttgc aaagatactc ctaattagcc tggctagatt agtttgtaaa ttccttgttg    1260
atgtgtcgtc tcagctttaa gctgcagaca tgctagcaag taacaacacg attagtacgt    1320
agtaatgtgg ttcttgatta tgagctgggg gtcttaacct tttttgtgtg acaagcaaga    1380
gaagaggatt tgggtacaat gtaatcctgt tcttccgctt tcgaaaaaaa aaaacatata    1440
gcttcacgtg cct                                                      1453
```

<210> SEQ ID NO 2
<211> LENGTH: 326
<212> TYPE: PRT
<213> ORGANISM: Oryza sativa

<400> SEQUENCE: 2

Met Thr Ser Ser Met Ser Pro Ala Pro Ala Pro Ala Tyr Ala Gln Val
1               5                   10                  15

Met Glu Asp Met Glu Lys Gly Lys Glu Leu Ala Ala Gln Leu Gln Gly
            20                  25                  30

Leu Leu Arg Asp Ser Pro Glu Ala Gly Arg Phe Val Asp Gln Ile Leu
        35                  40                  45

His Thr Phe Ser Arg Ala Met Arg Ala Leu Asp Lys Ala Ala Val Ser

|     |     |     |     | 50  |     |     |     |     | 55  |     |     |     |     | 60  |     |
| --- | --- | --- | --- | --- | --- | --- | --- | --- | --- | --- | --- | --- | --- | --- | --- | --- |
| Ala | Ala | Gly | Gly | Glu | Gly | Ser | Glu | Val | Gln | Ser | Glu | Val | Thr | Cys | Gly |
| 65  |     |     |     |     | 70  |     |     |     |     | 75  |     |     |     |     | 80  |

Gly Gly Ala Ser Ala Gly Gly Lys Arg Lys Ala Pro Ala Ala Asp Arg
                85                  90                  95

Lys Ala Asn Cys Arg Arg Thr Gln Gln Ser Ser Gly Asn Ser Val
                100                 105                 110

Val Val Lys Asn Leu Asp Asp Gly Gln Ala Trp Arg Lys Tyr Gly Gln
                115                 120                 125

Lys Glu Ile Gln Asn Ser Lys His Pro Lys Ala Tyr Phe Arg Cys Thr
            130                 135                 140

His Lys Tyr Asp Gln Leu Cys Thr Ala Gln Arg Gln Val Gln Arg Cys
145                 150                 155                 160

Asp Asp Asp Pro Ala Ser Tyr Arg Val Thr Tyr Ile Gly Glu His Thr
                165                 170                 175

Cys Arg Asp Pro Ala Thr Ala Pro Ile Ile Ala Ala His Val Ile His
                180                 185                 190

Gln Val Ala Ala Gly Asp Asn Asp Asp Gly Cys Gly Gly Leu Gln Ala
            195                 200                 205

Gly Ser Arg Leu Ile Ser Phe Val Ala Ala Pro Ala Ala Pro Val Asp
210                 215                 220

Ala Ala Ala Ala Pro Thr Thr Ser Thr Ile Thr Thr Val Thr Ala Pro
225                 230                 235                 240

Gly Pro Leu Leu Gln Pro Leu Lys Val Glu Gly Val Gly Ser Ser
                245                 250                 255

Asp Gln Glu Glu Val Leu Ser Ser Leu Thr Pro Gly Ser Ser Ala Ala
                260                 265                 270

Arg Gly Gly Gly Gly Gly Val Ala Gly Pro Phe Gly Pro Asp
                275                 280                 285

Gln Gly Asp Val Thr Ser Ser Leu His Trp Ser Tyr Asp Ala Val Ala
            290                 295                 300

Gly Met Glu Phe Phe Lys Asn Asp Glu Val Val Phe Asp Leu Asp Asp
305                 310                 315                 320

Ile Met Gly Leu Ser Phe
                325

```
<210> SEQ ID NO 3
<211> LENGTH: 43
<212> TYPE: DNA
<213> ORGANISM: Artificial Sequence
<220> FEATURE:
<223> OTHER INFORMATION: An artificially synthesized oligonucleotide
      sequence

<400> SEQUENCE: 3
gatctggcca aatcggccgg taccggatcc gcggccgcga gtc                    43

<210> SEQ ID NO 4
<211> LENGTH: 35
<212> TYPE: DNA
<213> ORGANISM: Artificial Sequence
<220> FEATURE:
<223> OTHER INFORMATION: An artificially synthesized oligonucleotide
      sequence.

<400> SEQUENCE: 4
cgcggccgcg gatccggtac cggccgattt ggcca                             35
```

US 8,373,021 B2

IMPROVING DISEASE RESISTANCE IN PLANTS BY INTRODUCING TRANSCRIPTION FACTOR GENE

This application is a U.S. national entry of International Application No. PCT/JP2006/310542, filed on May 26, 2006, which claims priority to Japanese Patent Application No. 2005-154731, filed on May 26, 2005.

TECHNICAL FIELD

The present invention relates to genes that function to improve disease resistance in plants as well as to transformed plants that comprise such genes and have improved disease resistance. Furthermore, the present invention relates to methods for improving disease resistance in plants using the genes.

BACKGROUND ART

In crop production, there is a steady demand for stable production of high quality plants and reduction of pesticide dependency. To that end, researchers are actively improving, breeding, and developing plants resistant to pests and pathogenic bacteria through useful plant biotechnologies, such as plant cell fusion and recombinant DNA techniques. Transformed plants resistant to herbicides (Patent Document 1), viruses (Patent Document 2), and pests (Patent Document 3) have been already produced using recombinant DNA techniques. Furthermore, several species of transformed plants resistant to plant pathogenic bacteria, such as the following, have been produced: a transformed plant showing resistance to a pathogenic filamentous fungus, produced by introducing a gene encoding an enzyme that inactivates a toxin produced by the pathogenic filamentous fungus (Non-patent Document 1); a transformed plant showing resistance to at least one pathogenic bacterium, produced by introducing a gene encoding an anti-bacterial protein derived from an insect (Patent Document 4); a transformed plant resistant to complex diseases, produced by introducing a gene derived from *Brassica rapa* L. var. *perviridis*) (Patent Document 5); a method for producing a plant resistant to multiple diseases using the thionine gene (Patent Document 6); and a method for producing a plant resistant to complex diseases using an acidic thaumatin-like protein gene (Patent Document 7). However, it is generally accepted that disease resistance obtained by introducing a single resistance gene is not sufficiently effective. Furthermore, some of the introduced genes have harmful effects on the growth, fertility and such of transformants, thereby hindering their practical application.

WRKY transcription factors have been reported to be involved in disease resistance of dicotyledons such as *Arabidopsis* (Non-patent Documents 2 to 7). In every case hitherto reported on *Arabidopsis* overexpressing the WRKY transcription factor genes, undesirable characters such as dwarfism, morphological abnormality, and leaf necrosis are reported (WRKY6: dwarfism, reduced apical dominance, leaf necrosis; AtWRKY18: growth inhibition, dwarfism, seed reduction; WRKY70: morphological abnormality, dwarfism). Furthermore, the WRKY transcription factors form a superfamily (about 100 members in rice), which is structurally classified into three groups. Some WRKY transcription factors have been suggested to be involved in morphogenesis and secondary metabolism apart from disease resistance, and each WRKY transcription factor is thought to have an individual function (Non-patent Document 8). The OsWRKY genes of rice have been reported to be involved in ABA-responsive gene expression in aleurone layer; however, the function of these genes in the context of disease resistance is not disclosed in this report (Non-patent Document 9). To date, there have been no reports on the improvement of plant disease resistance by an OsWRKY gene of rice.

Prior art references related to the present invention are listed below.

[Patent Document 1] Japanese Patent Application Kokai Publication No. (JP-A) H2-186925 (unexamined, published Japanese patent application)
[Patent Document 2] JP-A H4-330233
[Patent Document 3] JP-A H3-247220
[Patent Document 4] JP-A H7-250685
[Patent Document 5] JP-A 2004-329215
[Patent Document 6] JP-A 2003-88379
[Patent Document 7] JP-A 2003-199448
[Non-patent Document 1] Windhovel, U., Geiges, B., Sandmann, G. and Boger, P. (1994) Expression of *Erwinia uredovora* Phytoene Desaturase in *Synechococcus* PCC7942 Leading to Resistance against a Bleaching Herbicide. Plant Physiol. 104, 119-125.
[Non-patent Document 2] Kalde, M., Barth, M., Somssich, I. E. and Lippok, B. (2003) Members of the *Arabidopsis* WRKY group III transcription factors are part of different plant defense signaling pathways. Mol. Plant. Microbe Interact. 16, 295-305.
[Non-patent Document 3] Li, J., Brader, G. and Palva, E. T. (2004) The WRKY70 transcription factor: a node of convergence for jasmonate-mediated and salicylate-mediated signals in plant defense. Plant Cell 16, 319-331.
[Non-patent Document 4] Robatzek, S., and Somssich, I. E. (2002) Targets of AtWRKY6 regulation during plant senescence and pathogen defense. Genes Dev. 16, 1139-1149.
[Non-patent Document 5] Yu, D., Chen, C. and Chen, Z. (2001) Evidence for an important role of WRKY DNA binding proteins in the regulation of NPR1 gene expression. Plant Cell 13, 1527-1540.
[Non-patent Document 6] Chen, C. and Chen, Z. (2002) Potentiation of developmentally regulated plant defense response by AtWRKY18, a pathogen-induced *Arabidopsis* transcription factor. Plant Physiol. 129, 706-716.
[Non-patent Document 7] Asai, T., Tena, G., Plotnikova, J., Willmann, M. R., Chiu, W. L., Gomez-Gomez, L., Boller, T., Ausubel, F. M., and Sheen, J. (2002). MAP kinase signaling cascade in *Arabidopsis* innate immunity. Nature 415, 977-983.
[Non-patent Document 8] Eulgem, T., Rushton, P. J., Robatzek, S., and Somssich, I. E. (2000). The WRKY superfamily of plant transcription factors. Trends in Plant Sci. 5, 199-206.
[Non-patent Document 9] Xie, Z., Zhang, Z. L., Zou, X., Huang, J., Ruas, P., Thompson, D. and Shen, Q. J. (2005) Annotations and Functional Analyses of the Rice WRKY Gene Superfamily Reveal Positive and Negative Regulators of Abscisic Acid Signaling in Aleurone Cells. Plant Physiol. 137, 176-189.

DISCLOSURE OF THE INVENTION

Problems to be Solved by the Invention

The present invention was achieved in view of the above circumstances. An objective of the present invention is to provide genes that function to improve plant disease resistance as well as to transformed plants that comprise such genes and have improved disease resistance. Another objective of the present invention is to provide methods for improving plant disease resistance, which comprise the step of expressing the genes in plant cells. A further objective of the present invention is to provide pharmaceutical agents that improve disease resistance in plants, such agents comprising as active ingredients the genes of the present invention.

Means for Solving the Problems

In order to solve the aforementioned problems, the present inventors analyzed genes involved in plant disease resistance. As a result, the transcription factor gene OsWRKY45, which is induced in leaf blades of rice plants by activating the systemic acquired resistance (SAR) that plants inherently have, i.e., by treating rice plants with benzothiadiazole (hereinafter may be abbreviated as BTH), which is an agent considered to induce disease resistance in plants, was discovered. It was further discovered that resistance to blast disease and bacterial leaf blight in rice could be markedly improved by reintroducing the above gene into rice plants and constitutively expressing the same. Moreover, it was also found that OsWRKY45 overexpression had relatively little effect on rice plant growth, and that disease resistance in rice plants could be enhanced with little sacrifice of growth by selecting an appropriate line to be transformed. BTH potentiates the ability of plants themselves so that their inherent resistant reactions are shown effectively when they are infected with pathogens. From the facts that OsWRKY45 overexpression has little influence on plant growth despite conferring a high disease resistance, and that expression characteristics of the PR gene in OsWRKY45-overexpressing plants are similar to those in the case of BTH treatment, OsWRKY45 overexpression is thought to fairly mimic BTH action. Therefore, OsWRKY45 is considered to be functionally different from other WRKY genes.

The OsWRKY45 gene has been reported to be involved in the control of ABA-inducible gene expression; however, there is no disclosure of its BTH-responsiveness or disease resistance, nor has there been reports of enhanced disease resistance in a monocotyledon (rice) by introducing a transcription factor gene.

Although the improvement of disease resistance by introducing a resistance gene has traditionally involved the introduction of a single resistance gene (worker gene), such a procedure has generally been considered insufficient for improving disease resistance. In the present invention, it is thought that the introduction of a transcription factor gene uniformly induces the expression of a plurality of resistance genes (worker genes) that are controlled downstream of the transcription factor gene, thereby resulting in a strong expression of pathogen resistance. To date, there have been no reports that the simultaneous expression of a plurality of resistance-associated genes are induced by a transcription factor so as to improve disease resistance in rice, such as is disclosed herein.

Thus, the present inventors succeeded in isolating a transcription factor gene that improves plant disease resistance. Furthermore, they succeeded in improving disease resistance in plants by overexpressing the transcription factor gene in plant bodies, thereby completed the present invention.

More specifically, the present invention provides the following [1] to [17]:

[1] a DNA of any one of the following (a) to (d), wherein the DNA encodes a plant-derived protein that functions to improve plant disease resistance:
(a) a DNA encoding a protein comprising the amino acid sequence of SEQ ID NO: 2,
(b) a DNA comprising a coding region of the nucleotide sequence of SEQ ID NO: 1,
(c) a DNA encoding a protein comprising an amino acid sequence having one or more amino acid substitutions, deletions, additions, and/or insertions in the amino acid sequence of SEQ ID NO: 2, and
(d) a DNA that hybridizes to a DNA comprising the nucleotide sequence of SEQ ID NO: 1 under a stringent condition;

[2] the DNA of [1], wherein the plant is derived from a monocotyledon;

[3] the DNA of [1], wherein the plant disease is a filamentous fungous disease;

[4] the DNA of [1], wherein the plant disease is a bacterial disease;

[5] a vector comprising the DNA of any one of [1] to [4];

[6] a host cell into which the vector of [5] has been introduced;

[7] a plant cell into which the vector of [5] has been introduced;

[8] a transformed plant comprising the plant cell of [7];

[9] a transformed plant which is a progeny or a clone of the transformed plant of [8];

[10] a propagation material of the transformed plant of [8] or [9];

[11] a method for producing a transformed plant, which comprises the step of introducing the DNA of any one of [1] to [4] into a plant cell and regenerating a plant body from the plant cell;

[12] a protein encoded by the DNA of any one of [1] to [4];

[13] a method for preparing the protein of [12], which comprises the step of culturing the host cell of [6] and recovering a recombinant protein from the cell or a culture supernatant thereof;

[14] an antibody that binds to the protein of [12];

[15] a polynucleotide comprising at least 15 consecutive nucleotides that are complementary to the nucleotide sequence of SEQ ID NO: 1 or the complementary sequence thereof;

[16] a method for improving plant disease resistance, which comprises the step of expressing the DNA of any one of [1] to [4] in a cell of a plant body; and

[17] a pharmaceutical agent for improving plant disease resistance, which comprises as an active ingredient the DNA of any one of [1] to [4] or the vector of [6].

BRIEF DESCRIPTION OF THE DRAWINGS

FIG. 3 is composed of photographs and a graph demonstrating the blast disease resistance in growth chamber grown rice plants that overexpress the OsWRKY45 gene. Panel A is composed of photographs depicting blotch formation on the fourth leaf on day 7 after inoculation of an OsWRKY45-overexpressing rice plant line (OsWRKY45-ox) and non-transformed rice plants at the 4-leaf stage with a blast disease fungus (race 007). Panel B is a graph depicting the results of counting the number of blotches classified into progressive blotches and arrested blotches on the fourth leaf on day 7 after the inoculation of four lines of OsWRKY45-overexpressing rice plants at the 4-leaf stage with a blast disease fungus (race 007).

FIG. 9 is composed of photographs and a graph showing the bacterial leaf blight resistance in OsWRKY-overexpressing rice plants. Panel A is composed of photographs depicting bacterial leaf blight blotches in non-transformed rice plants and OsWRKY-overexpressing rice plants. Symptoms of the eighth leaf of five rice plants re shown for each type. Panel B depicts lengths of bacterial leaf blight blotches in non-transformed and OsWRKY-overexpressing rice plants. Means±standard deviations of blotch lengths on the eighth leaves of 12 non-transformed rice plants and 11 OsWRKY-overexpressing rice plants are shown.

BEST MODE FOR CARRYING OUT THE INVENTION

Figure 1:
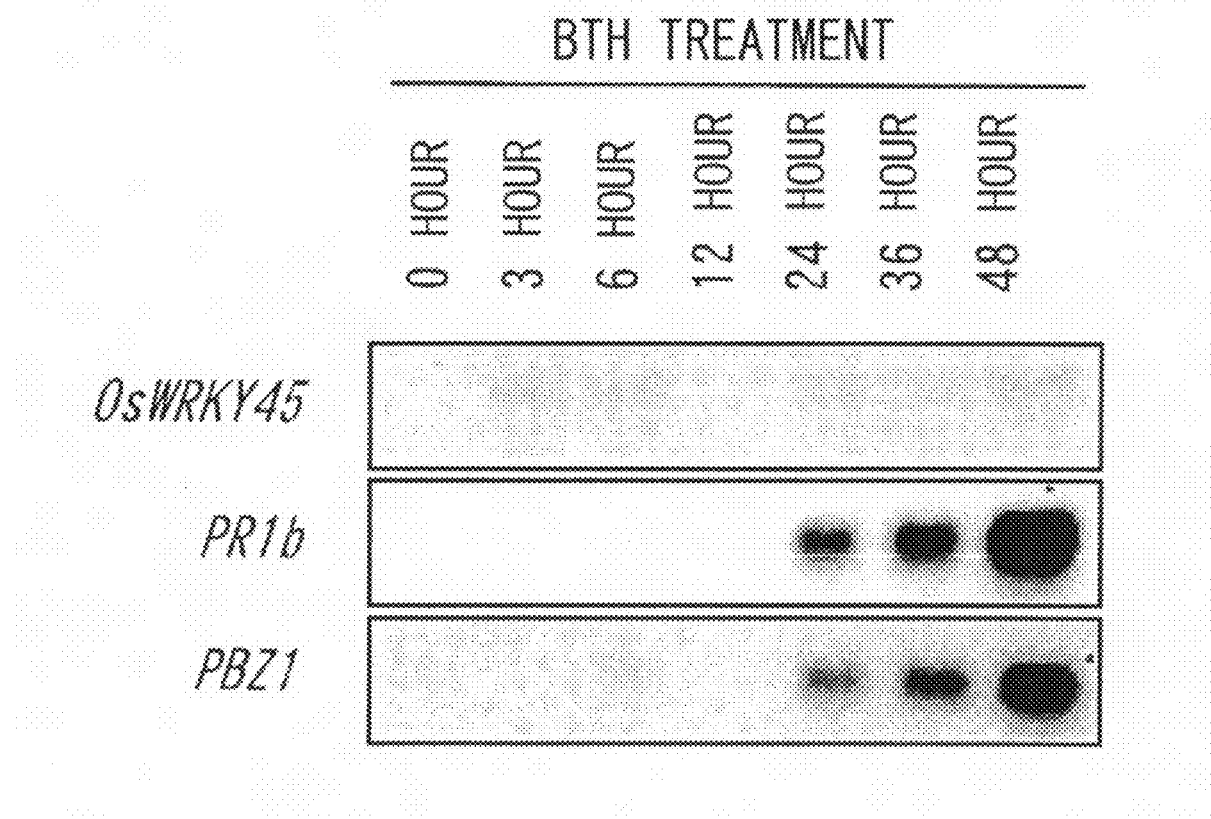
FIG. 1 depicts the induction of OsWRKY45 gene expression by BTH treatment. Rice plants at the 3.5-leaf stage were treated with BTH, and RNAs were prepared from leaves over time and subjected to Northern analysis. For comparison, two types of PR genes (PR1b and PBZ1) were also examined for induction of expression.

The present invention provides DNAs encoding plant-derived proteins that function to improve plant disease resistance.

In the context of the present invention, the phrase "plant disease" refers to any physiological disorder in plants which is caused by pathogens such as filamentous fungi (mainly molds), bacteria, or viruses, and which may reduce agricultural production and damage ecological environment. Pathogens are not particularly limited, and examples of diseases caused by pathogens include Actinomycetes, algae, and phytoplasmas (plant pathogenic microorganisms), in addition to the aforementioned three pathogens.

In the context of the present invention, plants which develop a disease are not particularly limited; however, they are preferably monocotyledons, more preferably gramineous plants, and most preferably rice plants.

Hereinafter, three typical pathogens of plant diseases (filamentous fungi, bacteria, and viruses) and symptoms of the diseases caused by these pathogens are described. Although a "disease" in the context of the present invention is not particularly limited, it may be any one of the diseases described below.

Filamentous fungi are microorganisms composed of multicellular "hyphae" that proliferate by forming spores. Since they have a rigid cell wall of chitin, they are considered to be highly resistant to drugs. Based on their shape and characteristics, filamentous fungi are classified as Phycomycetes (molds), Deuteromycetes (molds), Ascomycetes (molds and mushrooms), or Basidiomycetes (mushrooms). Phycomycetes are further divided into Mastigomycotinas and Zygomycetes.

Diseases caused by filamentous fingi present a variety of symptoms, including blotch formation on stem and leaf, rot, induction of dieback by impairing base of aerial part and root, formation of swellings such as gal, etc. As a major tendency of symptoms caused by filamentous fungi, growth of powdery molds and formation of granular black substances (sclerotia=mass of hyphae) are often observed in the affected sites. Typical filamentous fungous diseases in rice include the diseases caused by *Pseudocochliobolus lunatas*, *Rhizoctonia oryzae-sativae*, *Sarocladium attenuatum*, *Sclerophthora macrospora*, *Metaspharia albescens*, *Waitea circinata*, *Dreschslera gigantea*, *Entyloma dactylidis*, *Bipolaris oryzae*, *Chromelosporium fulvum*, *Magnaporthe salvinii*, *Peziza ostracoderma*, *Tilletia barclayana*, and *Rhizoctonia oryzae*. Rice blast disease, a symptom model in the Examples, also corresponds to a filamentous fungous disease; however, the symptoms are not limited thereto.

Bacteria are microorganisms composed of a single cell that have various shapes according to species. Bacteria swim to move in water, and invade plant bodies through wounds formed on the stub, stomata on the underleaf, etc. Bacterial diseases include those rotting stem and leaf, inducing an acute dieback, forming a tumorous swelling, etc. A common symptom includes a somewhat blurred contour of a blotch and yellowish discoloration in its periphery. Typical bacterial diseases in rice include rice bacterial brown stripe, rice bacterial leaf blight, rice bacterial palea browning, rice bacterial grain rot, and rice bacterial seedling blight. Rice bacterial leaf blight, a symptom model in the Examples, corresponds to a bacterial disease; however, the symptoms are not limited thereto.

Viruses are basically composed of nucleic acids and proteins, and have various shapes depending on species. Viruses have only either one of DNAs or RNAs, and cannot proliferate unless they invade cells of other organisms and utilize their nucleic acid synthesis/protein synthesis functions. Also known are viroids that resemble viruses in characteristics and cause similar diseases. Viroids contain only RNAs as nucleic acids and have no protein, and they are smaller than viruses in size. Diseases caused by viruses and viroids are, in most cases, accompanied by mosaic symptoms having pale patchy patterns in leaves and flowers, malformations such as dwarf and deformation, small brown necrotic spots, and such. In addition, a whole plant body may become yellow and dwarf, resulting in a significant growth inhibition. Typical viral diseases in rice include rice black-streaked dwarf, rice transitory yellowing disease, and rice dwarf disease.

In the context of the present invention, the phrase "improve plant disease resistance" means to confer a plant an effect in which symptoms of the aforementioned diseases do not occur or hardly occur by expressing the gene of the present invention in plant. This phrase also corresponds to an effect of improving resistance to pathogens and reducing their infection.

The effect of improving disease resistance may continuously last during the lifetime of plants or may be expressed for a certain period of time (for example, only at the early growth stage).

In addition, the disease resistance may be to a plurality of pathogens or only to a specific pathogen.

A "plant-derived protein having the function to improve plant disease resistance" can be preferably a transcription factor, or more preferably a transcription factor WRKY.

The nucleotide sequence of a cDNA of a transcription factor gene of the present invention and the amino acid sequence of a protein encoded by the cDNA are set forth in SEQ ID NOs: 1 and 2, respectively.

Since a transcription factor of the present invention functions to improve plant disease resistance, it is possible to grow a plant with pathogen resistance by transforming the plant with the DNA encoding the protein.

The DNAs of the present invention include genomic DNAs, cDNAs, and chemically synthesized DNAs. Genomic DNAs and cDNAs can be prepared by practices well used by those skilled in the art. For example, genomic DNAs can be prepared as follows: genomic DNAs are extracted from rice varieties that possess a transcription factor of the present invention, a genomic library is constructed (a plasmid, phage, cosmid, BAC, PAC or the like can be used as the vector) and developed, and colony or plaque hybridization can be carried out using probes prepared by using a DNA coding for a transcription factor protein of the present invention (for example, SEQ ID NO: 1) as a base. Alternatively, genomic DNAs can also be prepared by constructing primers specific to a DNA coding for a transcription factor protein of the present invention (for example, SEQ ID NO: 1), and then using these primers to carry out PCR. cDNAs can be prepared, for example, as follows: cDNAs are synthesized based on mRNAs extracted from rice varieties which include a gene coding for a transcription factor of the present invention, these cDNAs are inserted into λZAP vector or such, a cDNA library is prepared and developed, and a colony or plaque hybridization, or PCR is carried out in the same way as above.

The present invention also encompasses DNAs that encode proteins functionally equivalent to the transcription factor protein set forth in SEQ ID NO: 2. Herein, the phrase "functionally equivalent to a transcription factor protein" means the protein has the function to improve plant disease resistance. Such DNAs are preferably derived from monocotyledons, more preferably gramineous plants, and most preferably rice.

Such DNAs include mutants, derivatives, alleles, variants, and homologues that encode the proteins comprising, for example, an amino acid sequence having one or more amino acid substitutions, deletions, additions, and/or insertions in the amino acid sequence of SEQ ID NO: 2.

A method well known to those skilled in the art for preparing a DNA encoding a protein having a modified amino acid sequence includes, for example, the site-directed mutagenesis method. Mutation of the amino acid sequence of a protein due to the mutation of the coding nucleotide sequence may also occur in nature. Even DNAs encoding an amino acid sequence having one or more amino acid substitutions, deletions, or additions in the amino acid sequence encoding natural transcription factor proteins are included in DNAs of the present invention, so long as the DNAs encode proteins functionally equivalent to a natural transcription factor protein (SEQ ID NO: 2). Furthermore, even when nucleotide sequences are mutated, the mutations do not necessarily involve amino acid mutations in proteins (degeneracy mutation). Such degeneracy mutants are also included in DNAs of the present invention.

Whether or not a DNA encodes a protein that functions to improve plant disease resistance can be assessed by the method described below. The most common method is a procedure in which a known pathogen found to cause a disease is added to a plant introduced with the DNA and subsequent symptoms are examined while cultivating the plant in a growth chamber. Despite the addition of pathogen, when no disease symptom appears, it is shown that the introduced DNA encodes a protein having the function to improve plant disease resistance. Even when the disease symptoms are suppressed or reduced, it can be interpreted that a DNA encoding a protein having the function to improve plant disease resistance has been introduced.

Other methods well known to those skilled in the art for preparing DNAs encoding proteins functionally equivalent to the transcription factor protein set forth in SEQ ID NO: 2 include methods using hybridization techniques and polymerase chain reaction (PCR) techniques. That is, those skilled in the art can usually isolate DNAs highly homologous to a transcription factor gene from rice and other plants by using the nucleotide sequence of a transcription factor gene (SEQ ID NO: 1) or a portion thereof as a probe, or using an oligonucleotide that specifically hybridizes to the transcription factor gene (SEQ ID NO: 1) as a primer. Such DNAs encoding proteins functionally equivalent to a transcription factor protein that can be isolated by hybridization techniques and PCR techniques are also included in DNAs of the present invention.

In order to isolate such DNAs, hybridization reaction is preferably performed under stringent conditions. The stringent hybridization conditions in the present invention refer to the condition of 6M urea, 0.4% SDS, and 0.5×SSC or conditions of similar stringency. Isolation of more highly homologous DNAs can be expected using a more highly stringent condition, for example, a condition of 6M urea, 0.4% SDS, and 0.1×SSC. The DNAs thus isolated are thought to have a high homology to the amino acid sequence (SEQ ID NO: 2) of a transcription factor protein on the amino acid level. "High homology" refers to a sequence identity of at least 50% or more, more preferably 70% or more, or even more preferably 90% or more (for example, 95%, 96%, 97%, 98%, or 99% or more) in the whole amino acid sequence. The amino acid sequence identity or nucleotide sequence identity can be determined by using the BLAST algorithm developed by Karlin and Altschul (Proc. Natl. Acad. Sci. USA, 87: 2264-2268 (1990); Proc. Natl. Acad. Sci. USA, 90: 5873 (1993)). Programs referred to as BLASTN and BLASTX, which are based on the BLAST algorithm, have been developed (Altschul, S. F. et al. J. Mol. Biol. 215: 403 (1990)). To analyze nucleotide sequences by BLASTN, the parameters are set at, for example, score=100 and word length=12. On the other hand, the parameters used for the analysis of amino acid sequences by BLASTX are set at, for example, score=50 and word length=3. When using BLAST and Gapped BLAST programs, the default parameter is used for each program. Specific techniques for such analyses are known in the art.

DNAs of the present invention can be used, for example, to prepare recombinant proteins, and to produce transformed plants having improved disease resistance and so on.

Recombinant proteins are typically prepared by inserting DNAs encoding a protein of the present invention into an appropriate expression vector, introducing the vector into appropriate cells, culturing the transformed cells, and purifying the expressed proteins. Recombinant proteins can be expressed as fusion proteins with other proteins to make purification easier, for example, as fusion proteins with maltose-binding protein using *Escherichia coli* as a host (New England Biolabs, USA, vector pMAL series), as fusion proteins with glutathione-S-transferase (GST) (Amersham Pharmacia Biotech, vector pGEX series), or tagged with histidine (Novagen, pET series). The host cells are not particularly limited, so long as the cell is suitable for expressing the recombinant proteins. It is possible to use, for example, yeast, various plant or animal cells, insect cells or such in addition to the above-described *E. coli*. Vectors can be introduced into host cells by a variety of methods known to those skilled in the art. For example, introduction methods using calcium ions can be used for introduction into *E. coli*. Recombinant proteins expressed in the host cells can be purified and recovered from the host cells or the culture supernatant thereof by known methods in the art. When recombinant proteins are expressed as fusion proteins with the aforementioned maltose-binding protein or such, affinity purification can be carried out easily. Furthermore, using the procedures described below, transformed plants introduced with the DNAs of the present invention can be produced and the proteins of the present invention can be prepared from the plants.

Using the recombinant proteins thus obtained, antibodies that bind to the proteins can be prepared. For example, polyclonal antibodies can be prepared by immunizing animals used for immunizations, such as rabbits, with a purified protein of the present invention or a portion thereof, collecting blood after a certain period, and removing clots. Monoclonal antibodies can be prepared by fusing myeloma cells with antibody-producing cells of animals immunized with the above protein or peptide, isolating monoclonal cells (hybridomas) expressing a desired antibody, and recovering the antibodies from the cells. The antibodies thus obtained can be utilized to purify or detect the proteins of the present invention. The present invention encompasses antibodies that bind to the proteins of the present invention. These antibodies can be used to determine the expression sites of the proteins of the present invention in a plant body or to determine whether or not a plant species expresses a protein that improves plant disease resistance.

For producing transformed plants having improved plant disease resistance using the DNAs of the present invention, DNAs encoding the proteins of the present invention are inserted into appropriate vectors, and the vectors are introduced into plant cells to regenerate the transformed plant cells thus obtained. The transcription factor gene isolated by the present inventors has the function to improve plant disease resistance, and it is possible to introduce this transcription factor gene into an arbitrary plant variety and overexpress it, thereby improving disease resistance in that variety. This transformation requires an extremely short period of time compared to the conventional gene transfer by breeding, and also has an advantage in involving no alteration in other characteristics.

The present invention also provides vectors into which the above-described DNAs of the present invention have been inserted. The vectors of the present invention include, in addition to the aforementioned vectors used for producing recombinant proteins, vectors for expressing DNAs of the present invention in plant cells so as to produce transformed plants. Such vectors are not particularly limited, so long as they include a promoter sequence which can be transcribed in plant cells and a terminator sequence having a polyadenylation site required for stabilization of the transcription products. The vectors include, for example, "pBI121," "pBI221," and "pBI101" plasmids (all from Clontech). Vectors used for transformation of plant cells are not particularly limited so long as they can express the inserted gene in the cells. For example, it is also possible to use vectors carrying a promoter for constitutive gene expression in plant cells (e.g. the 35S promoter of cauliflower mosaic virus) or vectors carrying a promoter that is inducibly activated by external stimuli. Herein, "plant cells" include plant cells in various forms, for example, suspended cultured cells, protoplasts, leaf segments, and calluses.

Vectors of the present invention may comprise promoters for constitutively or inducibly expressing the proteins of the present invention. The promoters for constitutive expression include the 35S promoter of cauliflower mosaic virus, actin promoter of rice, and ubiquitin promoter of corn.

Furthermore, the promoters for inducible expression include those known to be expressed, for example, by external causes, such as infections with filamentous fungi, bacteria, or viruses, low temperature, high temperature, desiccation, ultraviolet irradiation, and diffusion of a particular compound. Such promoters include, for example, the promoter of rice chitinase gene and the promoter of tobacco PR protein gene, which are expressed by infections or invasions by filamentous fungi, bacteria, or viruses; the promoter of rice "lip 19" gene induced by low temperature; the promoters of rice "hsp80" gene and "hsp72" gene induced by high temperature; the promoter of *Arabidopsis thaliana* "rab16" gene induced by desiccation; the promoter of parsley chalcone synthase gene induced by ultraviolet irradiation; and the promoter of corn alcohol dehydrogenase gene induced under an anaerobic condition. Furthermore, the promoter of rice chitinase gene and the promoter of tobacco PR protein gene are also induced by a particular compound, such as salicylic acid, and the promoter of *Arabidopsis thaliana* "rab16" gene is also induced by the diffusion of abscisic acid, which is a phytohormone.

The present invention also provides transformed cells into which the vectors of the present invention have been inserted. Cells into which the vectors of the present invention are introduced include, in addition to the above-described cells used for producing recombinant proteins, plant cells for producing transformed plants. Plant cells are not particularly limited, and include, for example, cells of rice, *Arabidopsis*, corn, potato, and tobacco. Plant cells of the present invention include, in addition to cultured cells, cells in plant bodies as well as protoplasts, shoot primordia, multiple shoots, and hairy roots. The vectors can be introduced into plant cells using various methods known to those skilled in the art, such as the polyethylene glycol method, electroporation method, a method via *Agrobacterium*, and the particle gun method. Regeneration of a plant body from transformed plant cells can be performed by methods known to those skilled in the art depending on the type of plant cell. For example, in rice, several techniques for producing transformed plant bodies have been already established, including the following: a method for introducing a gene into a protoplast with polyethylene glycol to regenerate a plant body (suitable for indica rice varieties); a method for introducing a gene into a protoplast with electrical pulse to regenerate a plant body (suitable for japonica rice varieties); a method for directly introducing a gene into a cell by the particle gun method to regenerate a plant body; and a method for introducing a gene into a cell via *Agrobacterium* to regenerate a plant body and so on. These methods are widely used in the technical field of the present invention. In this invention, these methods can be preferably used.

Transformed plant cells can regenerate plant bodies by redifferentiation. Methods for redifferentiation vary depending on the type of plant cell. The methods include, for example, the method of Fujimura et al. (Plant Tissue Culture Lett. 2: 74 (1995)) for rice; the method of Shillito et al. (Bio/Technology 7: 581 (1989)) and the method of Gorden-Kamm et al. (Plant Cell 2: 603 (1990)) for corn; the method of Visser et al. (Theor. Appl. Genet. 78: 594 (1989)) for potato; the method of Nagata and Takebe (Planta 99: 12 (1971)) for tobacco; the method of Akama et al. (Plant Cell Reports 12: 7-11 (1992)) for *Arabidopsis*; and the method of Dohi et al. (JP-A H8-89113) for eucalyptus.

Once a transformed plant in which a DNA of the present invention has been introduced into the genome is obtained, its progeny can be obtained from the plant by sexual or asexual reproduction. It is also possible to obtain propagation materials (such as seeds, fruits, panicles, tubers, root tubers, stubs, calluses, and protoplasts) from the plant and its progenies or clones and to mass-produce the plant based on these materials. The present invention encompasses plant cells into which the DNAs of the present invention have been introduced; plants comprising such plant cells, progenies and clones of the plants as well as propagation materials of the plants and their progenies and clones.

The plants having improved disease resistance thus produced have improved pathogen resistance compared to wild-type plants. For example, it was found that the plants into which the DNA encoding a transcription factor OsWRKY45 had been introduced showed extremely high resistance to the blast fungus. Using the techniques of the present invention enables pesticide-free production of rice, which is a useful agricultural product, and may lead to the prevention of environmental destruction and improved productivity.

The present invention also provides polynucleotides comprising at least 15 consecutive nucleotides complementary to the nucleotide sequence of SEQ ID NO: 1 or its complementary sequence. Herein, the term "complementary sequence" refers to the sequence of the other strand relative to the sequence of one strand in a double-stranded DNA including A:T and G:C base pairs. Furthermore, the term "complementary" is not limited to the case of a completely complementary sequence in a region of at least 15 consecutive nucleotides, and may refer to at least 70%, preferably at least 80%, more preferably 90%, and even more preferably 95% or more of identity in nucleotide sequence. Such DNAs are useful as probes for detecting or isolating the DNAs of the present invention, or as primers for amplification.

The present invention relates to pharmaceutical agents for improving plant disease resistance, which comprise the DNAs or the vectors as active ingredients.

Pharmaceutical agents of the present invention may be mixed with, in addition to the DNAs or vectors as active ingredients, for example, sterilized water, physiological saline, vegetable oils, surfactants, lipids, solubilizers, buffering agents, preservatives and so on, if necessary.

All prior art references cited herein are incorporated herein by reference.

EXAMPLES

Herein below, the present invention is specifically described with reference to Examples; however, is the invention should not be construed as being limited thereto.

Example 1

Detection of a Transcription Factor Gene Inducibly Expressed by BTH

In order to detect a transcription factor gene inducibly expressed by BTH, rice seedlings (3.5-leaf stage) on day 10 after seeding were treated with 0.5 mM BTH (in 0.01% Tween 20/0.5% acetone), and the RNAs prepared over time (12, 24, 72, and 120 hours after the treatment) from BTH-treated and mock-treated rice leaves were subjected to DNA microarray analysis with the rice 22K array (Agilent). As a result, a WRKY transcription factor gene (OsWRKY45, AK066255; SEQ ID NOs: 1 and 2) that is inducibly expressed by BTH treatment was found. Northern blot analysis showed that OsWRKY45 expression was induced within 3 hours after BTH treatment (FIG. 1).

Example 2

Preparation of High Expression Vector for OsWRKY45 Gene

Figure 2:
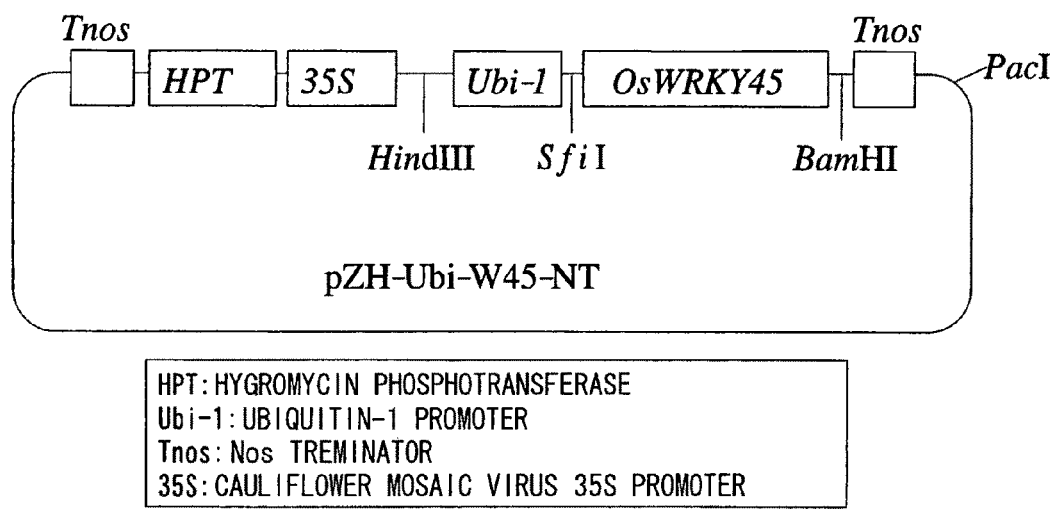
FIG. 2 depicts the structure of the DNA construct introduced into rice plants.

A vector for constitutively expressing the OsWRKY45 gene in plants was prepared by the following procedures. First, pUCAP/35S-NT (Kapoor et al., 2002) was cleaved with HindIII-BamHI, and an HindIII-BamHI fragment containing the corn Ubi-1 promoter derived from pAHC27 (Christensen and Quail, 1996) was inserted. Next, the obtained plasmid was cleaved at the BamHI-SacI sites between the Ubi-1 promoter and Nos terminator, and a complementary oligonucleotide (in which the top strand: 5'-GATCTGGCCAAATCG-GCCGGTACCGGATCCGCGGCCGCGAGTC (SEQ ID NO: 3) and the bottom strand: CGCGGCCGCGGATCCGG-TACCGGCCGATTTGGCCA (SEQ ID NO: 4) were annealed) was inserted to prepare pUCAP/Ubi-NT that includes both SfiI and BamHI sites between the Ubi-1 promoter and Nos terminator. pUCAP/Ubi-NT was cleaved with SfiI-BamHI, and an SfiI-BamHI fragment containing the full-length cDNA of the OsWRKY45 gene was inserted. Finally, this plasmid was cleaved with HindIII-PacI and inserted to pZH1 which had been cleaved with HindIII-PacI, to prepare a high expression vector for the OsWRKY45 gene, pZH-Ubi-W45-NT (FIG. 2).

Example 3

Introduction of a High Expression Vector for OsWRKY45 Gene into *Agrobacterium tumefaciens* EHA101 Strain In order to introduce the plasmid pZH-Ubi-W45-NT into *Agrobacterium tumefaciens* EHA101 strain, the strain was cultured with shaking in 5 ml of YEB medium (0.1% yeast extract, 0.5% meet extract, 0.5% peptone, 0.5% sucrose, and 0.05% $MgSO_4.7H_2O$) at 30° C. overnight. Next, 5 ml of the above culture was added to 200 ml of YEB medium in a 1-liter flask, and the mixture was further cultured at 30° C. for 5 to 6 hours. The cells were collected by centrifugation (at 4000 rpm for 5 min) and suspended in 100 ml of 10 mM Tris-HCl (pH 8.0). The suspension was centrifuged again, and the obtained cells were suspended in 2 ml of YEB medium. 200 μl of this suspension and 100 μl of a DNA solution containing 0.5 μg of pBE7133H-Thionin were mixed in a microcentrifuge tube, and the mixture was frozen in a dry ice/ethanol bath (for 5 min). The frozen mixture was then thawed in a 37° C. warm bath and left to stand for 25 min. Next, 2 ml of YEB medium was added and the mixture was cultured with shaking at 30° C. for 1 hour. The resulting culture solution (100 μl) was spread onto YEB medium containing kanamycin (50 μg/ml) and hygromycin (50 μg/ml), and cultured at 30° C. for about 36 hours to obtain resistant bacteria of *Agrobacterium tumefaciens* EHA101 strain. The thionine expression cassette in *Agrobacterium tumefaciens* EHA101 strain was isolated by the alkaline-SDS method and its presence and structure was confirmed by the restriction enzyme analysis.

Example 4

Production of Transformed Rice Plants

Sterilized rice seeds were cultured in MS medium containing 2 mg/ml of 2,4-dichlorophenoxyacetic acid (hereafter referred to as 2,4-D) (T. Murashige et al., Physiol. Plant, 15, 473 (1962)) at 27° C. for 2 weeks to form calluses. The calluses were transplanted to a co-culture medium (MS medium containing 2 mg/ml of 2,4-D and 1 g/l of casamino acid), and cultured at 27° C. On day 3 of the culture, the aforementioned *Agrobacterium tumefaciens* EHA101 strain carrying the thionine expression cassette was proliferated in YEB medium containing kanamycin and hygromycin, and then centrifuged. After the pelleted bacteria were suspended in LB medium, acetosyringone was added to prepare an *Agrobacterium tumefaciens* EHA101 strain solution for infection. This bacterial solution was warmed at 30° C. for 20 min. On day 4 of the culture, the above-described callus mass was added to the *Agrobacterium tumefaciens* EHA101 strain solution for infection, and the mixture was gently stirred at 30° C. for 15 min to infect the callus mass with the bacteria. The calluses were recovered 15 min later, and placed in the co-culture medium. The calluses were cultured at 27° C. for 3 days with a 16-hour day length, and then cultured in LB medium containing carbenicillin at 30° C. for one hour. Next, only the calluses were recovered and placed in a selection (growth) medium (co-culture medium containing 500 mg/l carbenicillin and 50 mg/l hygromycin). The calluses were cultured for 2 weeks with a 16-hour day length. A newly grown pale yellow calluses were transplanted to a selection (pretreatment-before-redifferentiation) medium (N6 medium containing 1 mg/l of 2,4-D, 0.5 mg/l of BAP, 2 g/l of casamino acid, 20 g/l of sucrose, 30 g/l of sorbitol, 500 mg/l of carbenicillin, and 100 mg/l of hygromycin), and after culturing for about 2 weeks, they were transplanted to a selection (redifferentiation) medium (N6 medium containing 0.01 mg/l of β-naphthaleneacetic acid (NAA), 0.1 mg/l of BAP, 1 g/l of casamino acid, 500 mg/l of carbenicillin, and 100 mg/l of hygromycin). Redifferentiated transformed rice plants were obtained in about 2 to 3 weeks.

Example 5

Examination of Changes in Blast Disease Resistance of OsWRKY45-Overexpressing Plant Bodies (in a Growth Chamber)

In order to examine changes in blast disease resistance of OsWRKY45-overexpressing plant bodies, OsWRKY45-overexpressing plant bodies and non-transformed rice seedlings (4-leaf stage) were inoculated with a blast fungus (race 007) on day 15 of growth in a growth chamber after seeding. The blotches present in a 5-cm long part near the center of the fourth leaf were counted 7 days later. Examination of the T1 generations in 4 lines of an OsWRKY45-overexpressing plant body (OsWRKY45-ox) showed that the number of blotches due to the blast disease infection was markedly decreased as compared to the non-transformed plant bodies (FIG. 3), and thus, that the blast disease resistance was improved. These transformants showed a little retardation of the early growth up to the 2-3 leaf stages after sprouting, and formed minor pseudo-blotches depending on the culture conditions, but otherwise grew similarly to non-transformants. Furthermore, no significant effect was observed on the spikelet fertility. These results suggest that OsWRKY45 overexpression has little influence on plant growth and such.

Example 6

Examination of Changes in Blast Disease Resistance of OsWRKY45-Overexpressing Plant Bodies (in a Greenhouse)

Figure 4:
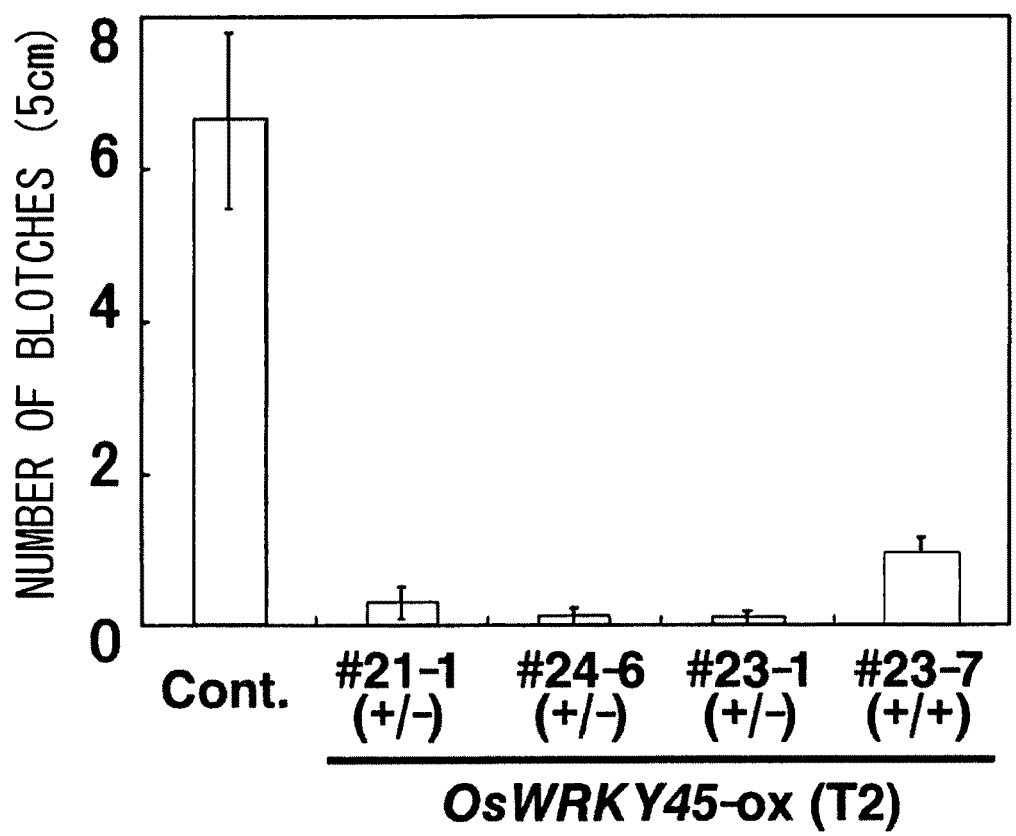
FIG. 4 is a graph depicting blast disease resistance of OsWRKY45-overexpressing rice plants grown in a greenhouse. OsWRKY45-overexpressing rice plants which had been seeded in March were grown in a greenhouse and inoculated with a blast disease fungus and then counted for the number of blotches, in a manner similar to that described in Example 5. Only progressive blotches were counted. The symbols in parentheses indicate whether the plant bodies are heterozygous (+/−) or homozygous (+/+) regarding the transgene.

Example 5 demonstrated that blast disease resistance was achieved in the OsWRKY45-overexpressing rice plants grown in a growth chamber. In this Example, in order to examine the effects of growth conditions on the expression of the resistance, OsWRKY45-overexpressing rice plants grown in a greenhouse were also examined for the blast disease resistance, in a manner similar to that described in Example 5. As a result, the OsWRKY45-overexpressing rice plants grown in a greenhouse also exhibited a markedly increased blast disease resistance similar to those grown in a growth chamber (FIG. 4).

Example 7

Examination of Effects of OsWRKY45 Overexpression on Rice Growth

Figure 5:
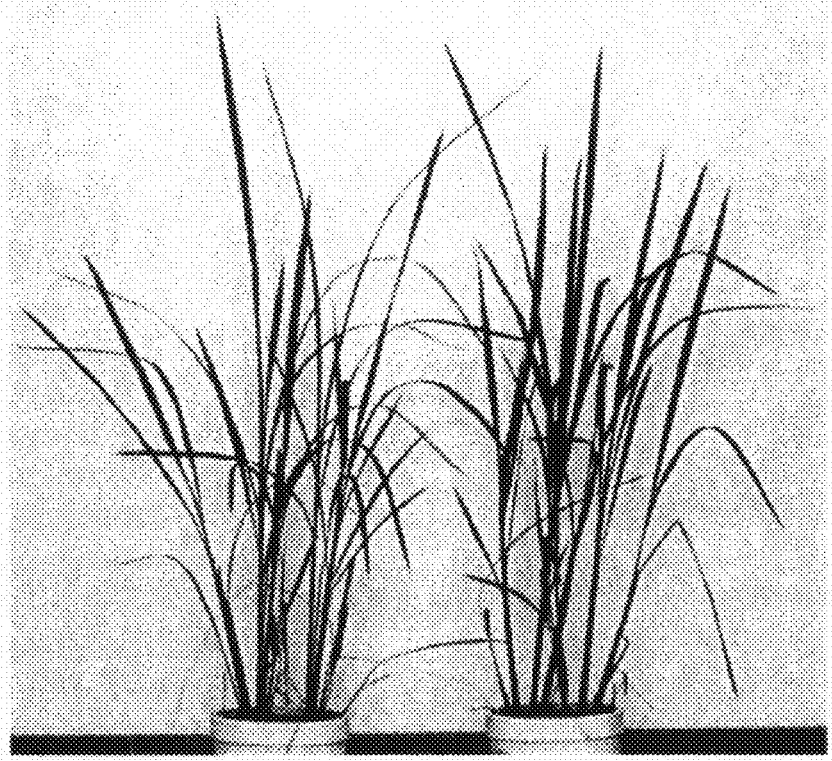
FIG. 5 is composed of a photograph and a diagram showing the growing condition of OsWRKY45-overexpressing rice plants. Panel A is a diagram depicting the results of examining the foliar age, plant length, and tiller number on week 7 after seeding of six to eight plant bodies in each of five T2 homozygous lines of OsWRKY45-overexpressing rice plants grown in a greenhouse. Panel B is a photograph depicting the appearances of the line (#23) that expressed the best growth and a wild type (WT) rice plant.

In order to examine the effects of OsWRKY45 overexpression on the growth of the transformants, T2 homozygous transformants (5 lines) having the blast disease resistance were grown in a greenhouse and the growth on week 7 after seeding was assayed. As a result, in three items—foliar age, plant length, and tiller number—, 4 lines (#15, 19, 21, and 24) showed a little growth retardation; however, #23 line showed almost the same values as the non-transformed plant bodies (FIG. 5). These results indicate that OsWRKY45 overexpression has a relatively minimal effect on rice growth, and that the blast disease resistance can be improved with little sacrifice of growth by selecting an appropriate line to be transformed. This is an important point in considering the utilization of the present gene at the practical level.

Example 8

Confirmation of Disease Resistance Marker PR Gene Expression

Figure 6:
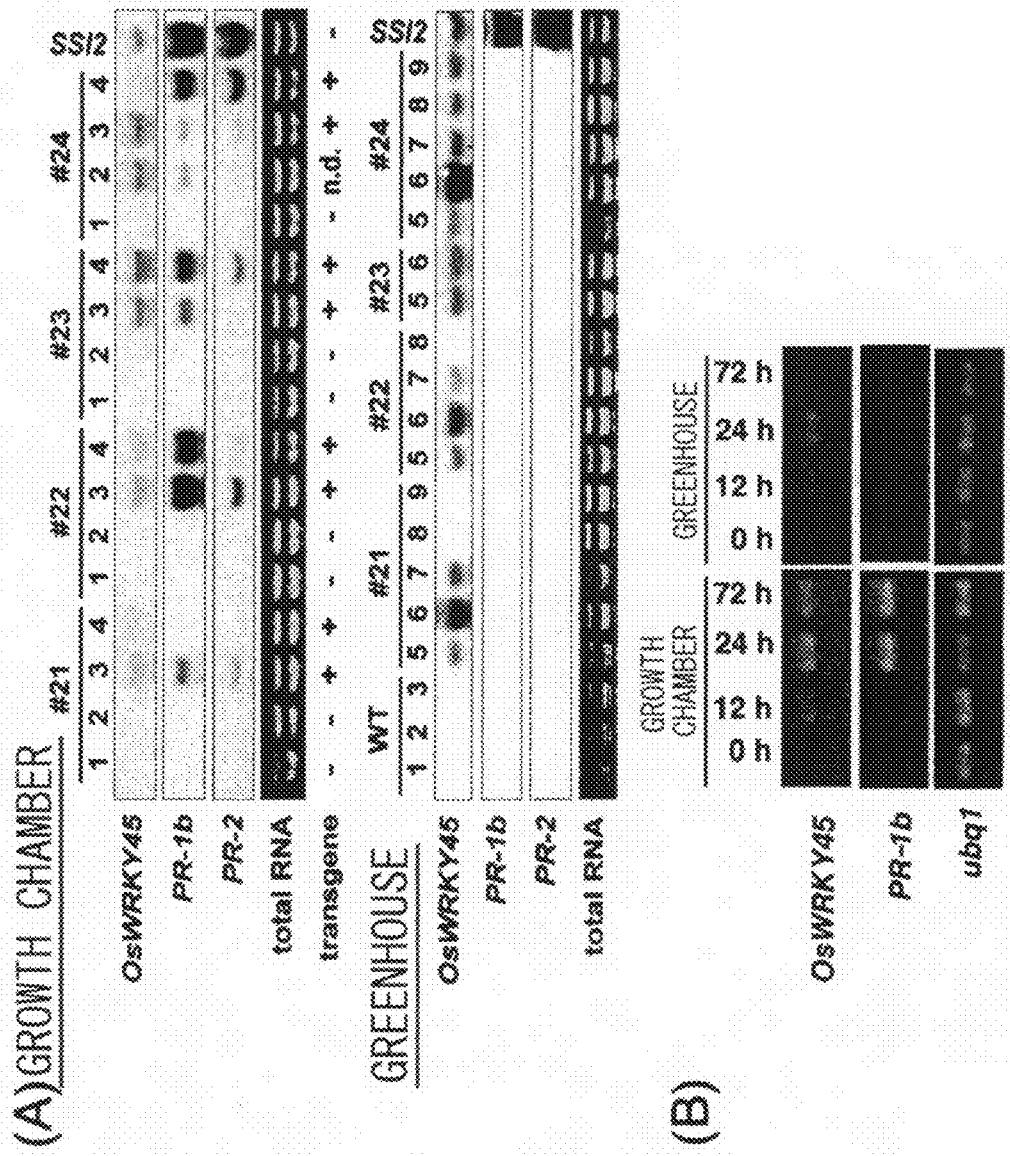
FIG. 6 is composed of photographs depicting the PR gene expression in OsWRKY45-overexpressing rice plants and BTH-treated wild-type rice plants grown in a growth chamber or in a greenhouse. Panel A is composed of photographs depicting the expression in OsWRKY45-overexpressing rice plants. Panel B is composed of photographs depicting the expression in BTH-treated wild-type rice plants.

Expression of PR gene is often used as a marker of disease resistant response. Therefore, the expression of two types of PR genes (PR1b and PR2) was examined in OsWRKY45-overexpressing rice plants grown in two different environments (in a growth chamber and greenhouse) (FIG. 6). Using each of cDNAs of OsWRKY45 (AK066255, nucleotide positions 1126 to 1426), PR-1b (AK107926, nucleotide positions 577 to 793), and PR2 (AK070677, nucleotide positions 1095 to 1295) as a probe, RNAs extracted from the rice plants grown under the different conditions were subjected to Northern blotting for expression analysis.

As a result, in the OsWRKY45-overexpressing rice plants grown in a growth chamber, both PR genes were constitutively expressed, while in the OsWRKY45-overexpressing rice plants grown in a greenhouse, no expression of either of the PR genes was recognized. These results are in contrast to those in which a high blast disease resistance was recognized, regardless of growth conditions (Examples 5 and 6). Similar dependence of the PR gene expression on growth conditions was also observed when non-transformed rice plants were treated with BTH. These results strongly support the suggestion that OsWRKY45 overexpression mimics BTH action (potentiation).

Example 9

Figure 7:
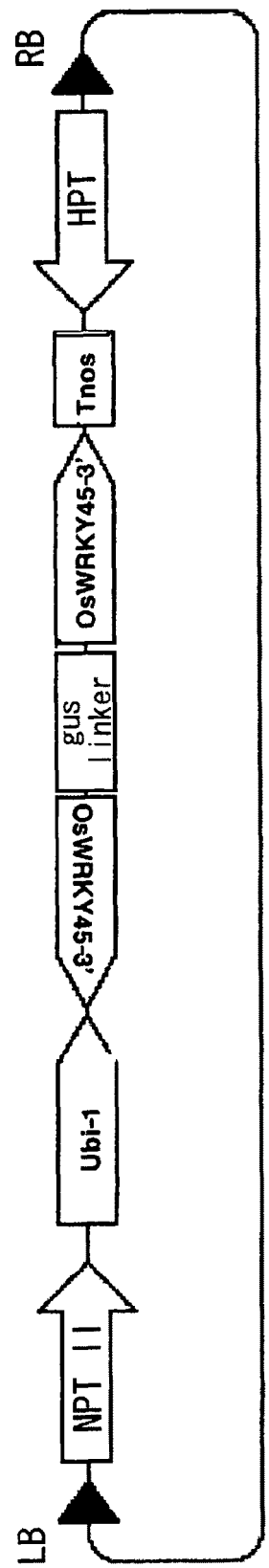
FIG. 7 depicts the structure of the plasmid used for OsWRKY45 RNAi.

Preparation of Plant Bodies in which OsWRKY45 Expression is Suppressed by RNAi and Blast Disease Assay In order to produce transformed rice plants in which OsWRKY45 expression is suppressed by RNAi, a plasmid was constructed by the following method. A portion of the 3'-noncoding region of OsWRKY45 cDNA (nucleotide positions 1047 to 1535) was amplified by PCR, and inserted downstream of the ubiquitin promoter in the pANDA vector (Miki, D. and Shimamoto, K. (2004). Simple RNAi vectors for stable and transient suppression of gene function in rice. Plant Cell Physiol. 45, 490-495; Miki, D., Itoh, R., and Shimamoto, K. (2005). RNA silencing of single and multiple members in a gene family of rice. Plant Physiol. 138, 1903-1913) so as to be placed in the order of the antisense sequence followed by the sense sequence sandwiching the linker sequence (GUS) between them (FIG. 7). The plasmid was constructed according to the procedure of Miki et al. (Miki, D. and Shimamoto, K. (2004). Simple RNAi vectors for stable and transient suppression of gene function in rice. Plant Cell Physiol. 45, 490-495: Miki, D., Itoh, R., and Shimamoto, K. (2005). RNA silencing of single and multiple members in a gene family of rice. Plant Physiol. 138, 1903-1913), except for using pDONR207 in place of pENTR as an intermediate vector.

Figure 8:
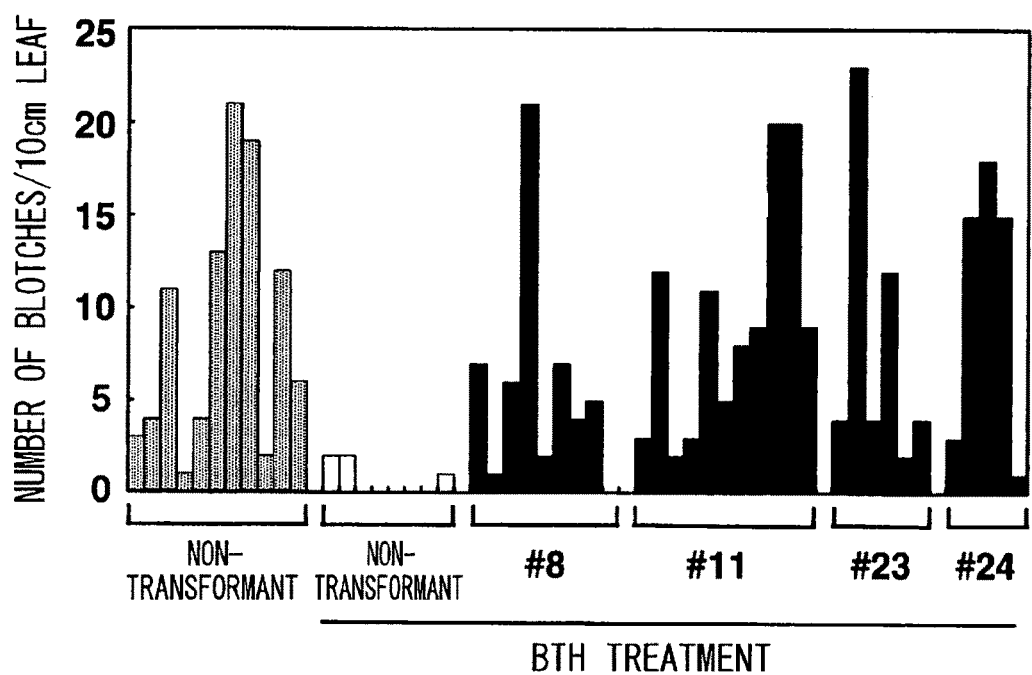
FIG. 8 is a graph depicting the results of inducing the blast disease resistance by BTH in rice plants in which OsWRKY45 expression is suppressed. A blast disease fungus was inoculated into non-transformed rice plants, either treated or not treated with BTH, and BTH-treated rice plants in which OsWRKY45 expression was suppressed. After seven days, the number of blotches on the 10-cm long central part of leaf blades was counted in each plant.

In order to examine the effect of suppression of OsWRKY45 expression on the blast disease resistance induced in rice by BTH treatment, non-transformed rice plants and transformed lines of rice plant in which the suppression of OsWRKY45 expression by RNAi had been confirmed were sprayed with 0.5 mM BTH at the 4-leaf stage, and then inoculated with a compatible blast disease fungus (race 007) 2 days later. After 7 days, the blotches present on the 10-cm long central part of leaf blades were counted in each plant body. Almost no blotches were observed in the BTH-treated non-transformed rice plants, while the BTH-treated rice plants in which OsWRKY45 expression was suppressed, showed a nearly equal number of blotches to that in non-treated, non-transformed rice plants. These results indicate that OsWRKY45 plays a principal role in inducing the blast disease resistance by BTH in rice (FIG. 8).

Example 10

Examination of Changes in Rice Bacterial Leaf Blight Resistance of OsWRKY45-Overexpressing Rice Plants The ability of OsWRKY45-overexpressing rice plants to show resistance to a rice leaf blight bacterium was assessed using the leaf clipping method (Kauffman, H. E., Reddy, A. P. K., Hsieh, S. P. Y., and Merca, S. D. (1973). An improved technique for evaluating resistance of rice varieties to *Xanthomonas oryzae*. Plant Disease Reporter 57, 537-541). That is, a rice leaf blight bacterium T7174 strain (a typical strain of race I) was slant-cultured in Wakimoto medium at 25° C. for 2 days, and diluted with sterilized distilled water to prepare a bacterial suspension at a concentration of $10^8$ cfu/ml as an inoculum. Inoculation was performed by clipping an about 5-cm long section from the tip of completely developed leaves in a test rice plant (48 days after seeding) with a pair of surgical scissors which had been soaked in the inoculum. The inoculated rice plants were managed in an isolated greenhouse to measure the blotch length from the leaf tip 2 weeks after the inoculation. As a result, in the OsWRKY45-overexpressing rice plants (T2 homozygotes), blotch progression was markedly suppressed compared to the control non-transformants (Nipponbare) (FIG. 9). These results revealed that the OsWRKY45-overexpressing rice plants also showed a strong resistance to rice bacterial leaf blight.

Example 11

Figure 10:
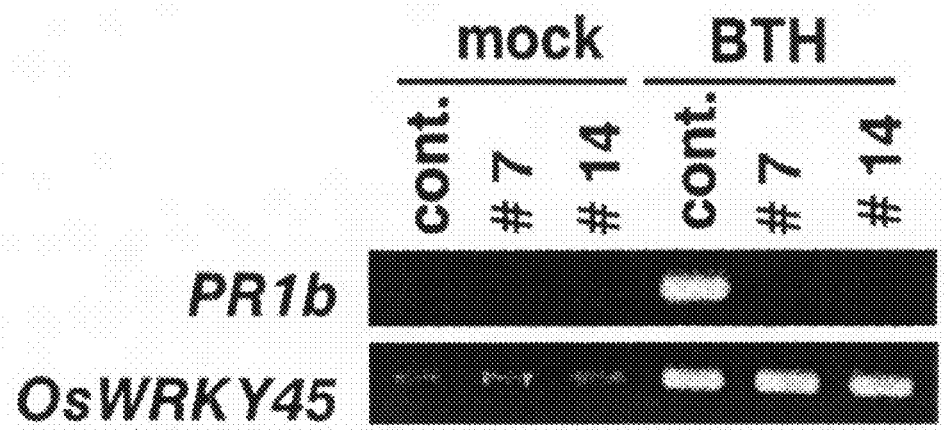
FIG. 10 is composed of photographs depicting OsWRKY45 expression in rice plants in which the expression of NH1, a rice NPR1 homolog, is suppressed by RNAi. Two lines (#7 and #14) in which the NH1 expression was suppressed by RNAi were BTH-treated or mock-treated to examine the induction of expression of PR1b and OsWRKY45 by RT-PCR.

OsWRKY45 Expression in Plants in which Expression of NH1, a Rice NPR1 Homolog, is Suppressed by RNAi Recently, it was reported that in *Arabidopsis thaliana*, the resistance to a filamentous fungus, *Erysiphe cichoracearum*, was enhanced by the introduction of WRKY70, a WRKY transcription factor (Li, J., Brader, G., Kariola, T., and Palva, E. T. (2006). WRKY70 modulates the selection of signaling pathways in plant defense. Plant J. 46, 477-491). Induction of *Arabidopsis thaliana* WRKY70 expression by salicylic acid is markedly reduced in NPR1, a mutant of NPR1 which is a key factor in the disease resistance signal transduction pathway. From these findings, WRKY70 is thought to be a transcription factor downstream of NPR1. Thus, for comparison of functions between WRKY70 and OsWRKY45, the induction of PR1b and OsWRKY45 expressions by BTH was examined in rice plants in which NH1, a rice NPR1 homolog (Chern, M., Fitzgerald, H. A., Canlas, P. E., Navarre, D. A., and Ronald, P. C. (2005). Overexpression of a rice NPR1 homolog leads to constitutive activation of defense response and hypersensitivity to light. Mol. Plant-Microbe Int. 18, 511-520) was suppressed by RNAi. As a result, it was shown that in the plants in which NH1 was suppressed by RNAi, the induction of PR1b expression by BTH was completely lost, while the induction of OsWRKY45 expression was not affected at all (FIG. 10). These results indicate that OsWRKY45 does not lie downstream of NH1, and that OsWRKY45 and WRKY70 are functionally different.

INDUSTRIAL APPLICABILITY

In the present invention, it was discovered that a rice transcription factor gene, OsWRKY45, is expressed in response to BTH, a disease preventive agent, and that blast disease resistance can be markedly enhanced by introducing this gene into rice plants and highly expressing it under the control of the ubiquitin promoter.

The OsWRKY45-introduced transformants showed only a little early growth retardation and the formation of minor pseudo-blotches without marked adverse effects on growth and spikelet fertility. Since the OsWRKY45 transformants have properties comparable to disease preventive agents such as BTH in both disease resistance effects and low side effects, their use may likely be developed into a practical technique.

Development and practical application of the methods of the present invention may enable pesticide-free production, thereby significantly contributing to economy and safety.

The invention claimed is:

1. A method for producing a transformed plant, which comprises the steps of introducing into a plant cell an isolated DNA sequence of any one of the following (a) to (c), wherein the DNA sequence encodes a plant-derived protein that functions to improve plant disease resistance compared to a wild type plant, and wherein the plant is a monocotyledon:
   (a) a DNA sequence encoding a protein comprising the amino acid sequence of SEQ ID NO: 2;
   (b) a DNA sequence comprising the coding region of the nucleotide sequence of SEQ ID NO: 1; and
   (c) a DNA sequence encoding a protein comprising an amino acid sequence having 95% or more identity to the amino acid sequence of SEQ ID NO: 2;
   regenerating a plant body from the plant cell; and
   selecting regenerated plants comprising said isolated DNA sequence with improved plant disease resistance comparable to a wild type plant and with only minor sacrifice of growth compared to a [benzothiadiazole (BTH)-treated] wild type plant.

2. A method for improving plant disease resistance, which comprises the steps of introducing into a plant cell an isolated DNA sequence of any one of the following (a) to (c), and expressing in said plant cell a DNA sequence of any one of the following (a) to (c), wherein the DNA sequence encodes a plant-derived protein that functions to improve plant disease resistance compared to a wild-type plant with only minor sacrifice of growth comparable to a [benzothiadiazole (BTH)-treated] wild type plant, wherein the DNA sequence is integrated into the genome of the cell, and wherein the plant is a monocotyledon:
   (a) a DNA sequence encoding a protein comprising the amino acid sequence of SEQ ID NO: 2;
   (b) a DNA sequence comprising the coding region of the nucleotide sequence of SEQ ID NO: 1; and
   (c) a DNA sequence encoding a protein comprising an amino acid sequence having 95% or more identity to the amino acid sequence of SEQ ID NO: 2; and
   selecting a plant cell comprising said isolated DNA sequence with improved plant disease resistance compared to a wild type plant cell.

3. The method of claim 1, wherein the plant disease is a filamentous fungous disease.

4. The method of claim 1, wherein the plant disease is a bacterial disease.

5. The method of claim 2, wherein the plant disease is a filamentous fungous disease.

6. The method of claim 2, wherein the plant disease is a bacterial disease.

7. A method for improving plant disease resistance, which comprises the steps of introducing into a plant cell an isolated DNA sequence of any one of the following (a) to (c), and expressing in said plant cell a DNA sequence of any one of the following (a) to (c) to produce a transgenic plant having one or more phenotype the is substantially the same as a wild type plant, wherein said phenotype is selected from the group consisting of foliar age, plant length, tiller number, and spikelet fertility, wherein the DNA sequence encodes a plant-derived protein that functions to improve plant disease resistance compared to a wild type plant, wherein the DNA sequence is integrated into the genome of the cell, and wherein the plant is a monocotyledon:
   (a) a DNA sequence encoding a protein comprising the amino acid sequence of SEQ ID NO: 2;
   (b) a DNA sequence comprising the coding region of the nucleotide sequence of SEQ ID NO: 1; and
   (c) a DNA sequence encoding a protein comprising an amino acid sequence having 95% or more identity to the amino acid sequence of SEQ ID NO: 2; and
   selecting a plant comprising said isolated DNA sequence with improved disease resistance compared to a wild type plant.

8. The method of claim 7, further comprising the step of selecting said transgenic plant having said one or more phenotype.

* * * * *

UNITED STATES PATENT AND TRADEMARK OFFICE
CERTIFICATE OF CORRECTION

PATENT NO. : 8,373,021 B2  
APPLICATION NO. : 11/919864  
DATED : February 12, 2013  
INVENTOR(S) : Takatsuji et al.

Page 1 of 1

It is certified that error appears in the above-identified patent and that said Letters Patent is hereby corrected as shown below:

In the Claims:

Column 21, line 19-20, claim 1,

Replace the mistaken word "comparable to a wild type" with the correct word "compared to a wild type".

Column 21, line 19-20, claim 1,

Delete the mistaken term "[benzothiadiazole (BTH)-treated]".

Column 21, line 28-29, claim 2,

Replace the mistaken term "comparable to a [benzothiadiazole (BTH)-treated] wild type" with the correct term "compared to a wild type".

Column 22, line 17, claim 7,

Replace the mistaken term "phenotype the is substantially" with the correct term "phenotype that is substantially".

Signed and Sealed this  
Sixteenth Day of July, 2013

Teresa Stanek Rea  
*Acting Director of the United States Patent and Trademark Office*